(12) United States Patent
Toyoda et al.

(10) Patent No.: US 11,454,640 B2
(45) Date of Patent: Sep. 27, 2022

(54) CULTURE MEDIUM PROCESSING SYSTEM AND METHOD WITH DEPROTEINIZATION IN A FILTRATION CONTAINER

(71) Applicant: SHIMADZU CORPORATION, Kyoto (JP)

(72) Inventors: Kenichi Toyoda, Kyoto (JP); Takashi Suzuki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 261 days.

(21) Appl. No.: 16/821,205

(22) Filed: Mar. 17, 2020

(65) Prior Publication Data

US 2020/0333369 A1    Oct. 22, 2020

(30) Foreign Application Priority Data

Apr. 18, 2019  (JP)  .............................. JP2019-079237

(51) Int. Cl.
| | | |
|---|---|---|
| *G01N 35/10* | (2006.01) | |
| *G01N 35/02* | (2006.01) | |
| *G01N 1/28* | (2006.01) | |
| *G01N 30/16* | (2006.01) | |
| *G01N 30/14* | (2006.01) | |
| *G01N 30/06* | (2006.01) | |
| *G01N 30/02* | (2006.01) | |

(52) U.S. Cl.
CPC ............ *G01N 35/1011* (2013.01); *G01N 1/28* (2013.01); *G01N 30/14* (2013.01); *G01N 30/16* (2013.01); *G01N 35/1002* (2013.01); *G01N 2030/027* (2013.01)

(58) Field of Classification Search
CPC .......... G01N 35/1011; G01N 35/1002; G01N 35/025; G01N 1/28; G01N 30/16; G01N 30/14; G01N 30/06; C12M 29/26
USPC ............................ 422/70; 436/161, 177–178
See application file for complete search history.

(56) References Cited

U.S. PATENT DOCUMENTS

| | | | | | |
|---|---|---|---|---|---|
| 5,466,669 A | * | 11/1995 | Konig | ..................... | C07K 14/79 |
| | | | | | 514/21.3 |
| 10,473,630 B2 | * | 11/2019 | Hanafusa | ............. | G01N 35/025 |

(Continued)

FOREIGN PATENT DOCUMENTS

| | | |
|---|---|---|
| EP | 3176576 A1 | 6/2017 |
| WO | 2016/017042 A1 | 4/2016 |

OTHER PUBLICATIONS

Teerlink, T et al, Journal of Chromatography B, 1997 694, 83-92.*

(Continued)

*Primary Examiner* — Arlen Soderquist
(74) *Attorney, Agent, or Firm* — Sughrue Mion, PLLC

(57) ABSTRACT

The culture medium processing system includes a controller (100) configured to control operation of a sample dispensing part (20), a reagent dispensing part (26) and a transport arm (24) to deproteinize a sample, wherein the controller (100) is configured to dispense a methanol solution into an empty filtration container (50) to perform a conditioning of a filtration filter (52) disposed in the filtration container (50), then dispense a sample into the filtration container (50), add an acetonitrile solution as a deproteinization agent to the sample in the filtration container (50), and then perform a filtration process in the filtration part (30).

12 Claims, 5 Drawing Sheets

(56) References Cited

U.S. PATENT DOCUMENTS

| | | | | |
|---|---|---|---|---|
| 2003/0216349 A1* | 11/2003 | Belardinelli | A61K 31/138 | 514/355 |
| 2004/0053922 A1* | 3/2004 | Ouellette | C07D 417/12 | 514/227.8 |
| 2005/0131059 A1* | 6/2005 | Wang | A61P 35/00 | 514/456 |
| 2006/0293283 A1* | 12/2006 | Kalla | A61P 1/04 | 514/263.2 |
| 2007/0092924 A1* | 4/2007 | Anderson | C12Q 1/37 | 435/68.1 |
| 2008/0280370 A1* | 11/2008 | Bramble, Jr. | C07F 9/3813 | 436/104 |
| 2008/0318322 A1* | 12/2008 | Akhlaghi | G01N 33/9493 | 436/43 |
| 2009/0299072 A1* | 12/2009 | Shapiro | C07C 59/72 | 548/134 |
| 2010/0105737 A1* | 4/2010 | Tanaka | A61P 31/10 | 546/256 |
| 2011/0085983 A1* | 4/2011 | Le | G01N 30/6004 | 424/9.2 |
| 2011/0281369 A1* | 11/2011 | Akhlaghi | G01N 33/9493 | 436/93 |
| 2011/0291004 A1* | 12/2011 | Kanda | H01J 49/26 | 250/288 |
| 2012/0046266 A1* | 2/2012 | Brasca | A61P 25/28 | 544/367 |
| 2013/0090372 A1* | 4/2013 | Budzik | C07D 295/084 | 564/504 |
| 2013/0164370 A1* | 6/2013 | Pumeranz | C07K 9/008 | 514/2.3 |
| 2013/0225836 A1* | 8/2013 | Stanton | C07D 223/08 | 548/541 |
| 2013/0231315 A1* | 9/2013 | Fadini | A61K 45/06 | 514/253.01 |
| 2013/0295597 A1* | 11/2013 | DeWitte | H01J 49/0413 | 435/23 |
| 2014/0243407 A1* | 8/2014 | Bley | A61P 1/04 | 560/163 |
| 2015/0087649 A1* | 3/2015 | Hunt, III | A61K 31/167 | 514/630 |
| 2015/0366839 A1* | 12/2015 | Lee | A61K 31/36 | 514/463 |
| 2016/0025606 A1* | 1/2016 | Oroskar | B01L 3/50255 | 422/534 |
| 2016/0370357 A1* | 12/2016 | Lucas | G01N 1/405 | |
| 2017/0107228 A1* | 4/2017 | Cuny | A61P 31/12 | |
| 2017/0168027 A1 | 6/2017 | Hanafusa et al. | | |
| 2018/0080858 A1* | 3/2018 | Richter | B01J 20/3274 | |
| 2018/0312462 A1* | 11/2018 | Shi | C07C 237/42 | |
| 2019/0070103 A1* | 3/2019 | Ameri | A61K 9/0021 | |
| 2020/0140482 A1* | 5/2020 | Nitta | G01N 1/4044 | |
| 2021/0072230 A1* | 3/2021 | Palmer | G01N 33/5014 | |

OTHER PUBLICATIONS

Biddlecombe, R. A. et al, Journal of Chromatography B, 1999, 734, 257-265.*
Rouan, M. C. et al, Journal of Pharmaceutical and Biomedical Analysis 2001, 25, 995-1000.*
Hou, W. et al., Journal of Chromatography B, 2004, 804, 263-267.*
Krynitsky, A. J. et al, Analytical Chemistry 2004, 76, 5518-5522.*
Bruce, S. J. et al, Analytical Chemistry 2009, 81, 3285-3296.*
Ferreiro-Vera, C. et al,Taianta 2011, 85, 1842-1847.*
Barri, T. et al, Analytica Chimica Acta 2012, 718, 47-57.*
Vuckovic, D., Analytical and Bioanalytical Chemistry 2012, 403, 1523-1548.*
Wohlfarth, A. et al, Journal of Mass Spectrometry 2012, 47, 778-785.*
Molinelli, A. R. et al, in Clinical Applications of Mass Spectrometry in Drug Analysis: Methods and Protocols, Methods in Molecular Biology, Garg, U. Ed, 2016, 1383, 39-47.*
Kiriazopoulos, E. et al, Drug Testing and Analysis 2017, 9, 1062-1072.*
Daskalaki, E. et al, Analytica Chimica Acta 2018, 1037, 338-350.*
Suzuki, T. et al, Spectrométrie de Masse 2018, 7, 7 pages.*
Kucerova, et al, Journal of Chromatography A 2019, 1607, paper 460390, 8 pages.*
Extended European Search Report dated Sep. 16, 2020 from the European Patent Office in Application No. 20163766.7.

* cited by examiner

CULTURE MEDIUM PROCESSING SYSTEM AND METHOD WITH DEPROTEINIZATION IN A FILTRATION CONTAINER

BACKGROUND OF THE INVENTION

1. Field of the Invention

The present invention relates to a culture medium processing system and a culture medium processing method of deproteinizing a culture medium used for cell culture.

2. Description of the Related Art

To determine the state of the cells in culture (differentiated/undifferentiated) the supernatant of the culture medium from the container during cell culture may be taken, and the culture medium may be deproteinized before liquid chromatography analysis. In order to deproteinize the culture medium, a preprocessing apparatus as disclosed in Patent Literature 1 is used.

CITATION LIST

Patent Literature

Patent Literature 1: WO 2016/017042 A1

SUMMARY OF THE INVENTION

The deproteinization process of the culture medium is performed using a filtration container provided with a filtration filter therein. In particular, the deproteinization process is performed by dispensing the conditioning agent into the filtration container and conditioning the filtration filter, dispensing the internal standard sample, the culture medium as a sample, and the deproteinization agent into the filtration container and stirring them, and after that, applying pressure to the inside of the filtration container to allow the liquid in the filtration container to pass through the filtration filter to collect the filtrate in a collection container.

In a conventional deproteinization process, the same type of organic solvent was used as a conditioning agent and a deproteinization agent. Since the culture medium used to culture cells varies depending on the type of cells, the amount of filtrate obtained (recovery rate) varied depending on the type of culture medium. Therefore, in the related art, it has been necessary to prepare a large amount of the culture medium to be prepared for measurement according to the type of the culture medium. However, a small amount of culture medium may be used for the culture, and it may be difficult to prepare the amount of the culture medium necessary for the measurement.

The present invention has been made in view of the above problems, and it is an object of the present invention to improve the recovery rate of the filtrate and make it possible to minimize the amount of a culture medium used for measurement.

The present inventors have found in the deproteinization process that a high recovery rate can be obtained irrespective of the type of culture medium by using a methanol solution as a conditioning agent, and using an acetonitrile solution as a deproteinization agent. The present invention has been made based on such knowledge.

The culture medium processing system according to the present invention includes an extraction device including a filtration container and a collection container. The filtration container has an open upper surface, a filtration filter, disposed inside the filtration container, for deproteinizing a culture medium for cell culture, and an extraction port, disposed at a lower end of the filtration container, for extracting a filtrate downward that has passed through the filtration filter. The collection container is for collecting the filtrate extracted from the extraction port of the filtration container by being disposed immediately below the filtration container. The culture medium processing system further includes an extraction device setting place at which the extraction device is set in an empty state; a sample container setting place at which sample containers containing culture medium to be deproteinized as samples are set; a reagent container setting place at which reagent containers containing at least a methanol solution and an acetonitrile solution respectively as reagents are set; a sample dispensing part configured to suck a sample from a sample container set at the sample container setting place and dispense the sucked sample into the filtration container disposed at a predetermined sample dispensing position; a reagent dispensing part configured to suck desired reagents from the reagent containers set at the reagent container setting place and to dispense the sucked reagents into the filtration container disposed at a predetermined reagent dispensing position; a filtration part including a filtration port at which the extraction device is set with the collection container disposed immediately below the filtration container, where the filtration part is configured to collect a filtrate into the collection container by performing a filtration process for a solution in the filtration container of the extraction device set at the filtration port; a transport arm configured to hold the filtration container and/or the collection container of the extraction device set at the extraction device setting place and to transport the held filtration container and/or the held collection container to the sample dispensing position, the reagent dispensing position, and the filtration part; and a controller configured to control operation of the sample dispensing part, the reagent dispensing part and the transport arm to deproteinize a sample. The controller is configured to perform conditioning for the filtration filter by dispensing a methanol solution into the empty filtration container, then to dispense a sample into the filtration container add the acetonitrile solution as a deproteinization agent to the sample in the filtration container, and then to perform the filtration process in the filtration part.

In a method of processing a culture medium using an extraction device according to the present invention, the extraction device includes a filtration container and a collection container. The filtration container has an open upper surface, a filtration filter, disposed inside the filtration container, for deproteinizing a culture medium for cell culture, and an extraction port, disposed at a lower end of the filtration container, for extracting a filtrate downward that has passed through the filtration filter. The collection container is for collecting the filtrate extracted from the extraction port of the filtration container by being disposed immediately below the filtration container. The method of processing the culture medium includes, in the sequence set forth, a conditioning step of dispensing a methanol solution into the empty filtration container to condition the filtration filter; a sample dispensing step of dispensing a culture medium as a sample into the filtration container; a deproteinization agent dispensing step of adding an acetonitrile solution as a deproteinization agent to the sample in the filtration container; and a filtration step of filtering a solution in the filtration container with the collection container disposed immediately below the filtration container to collect the filtrate in the collection container.

In the culture medium processing system according to the present invention, since a methanol solution is used as a conditioning agent for conditioning the filtration filter, and an acetonitrile solution is used as a deproteinization agent, the filtrate can be collected at a high recovery rate irrespective of the type of the culture medium as a sample, and the liquid volume of the culture medium used for the measurement can be made as small as possible.

In the culture medium processing method according to the present invention, since a methanol solution is used as a conditioning agent for conditioning the filtration filter, and an acetonitrile solution is used as a deproteinization agent, the filtrate can be collected at a high recovery rate irrespective of the type of the culture medium as a sample, and the liquid volume of the culture medium used for the measurement can be made as small as possible.

DETAILED DESCRIPTION OF THE INVENTION

Hereinafter, an embodiment of the culture medium processing system and the culture medium processing method will be described.

Figure 1:
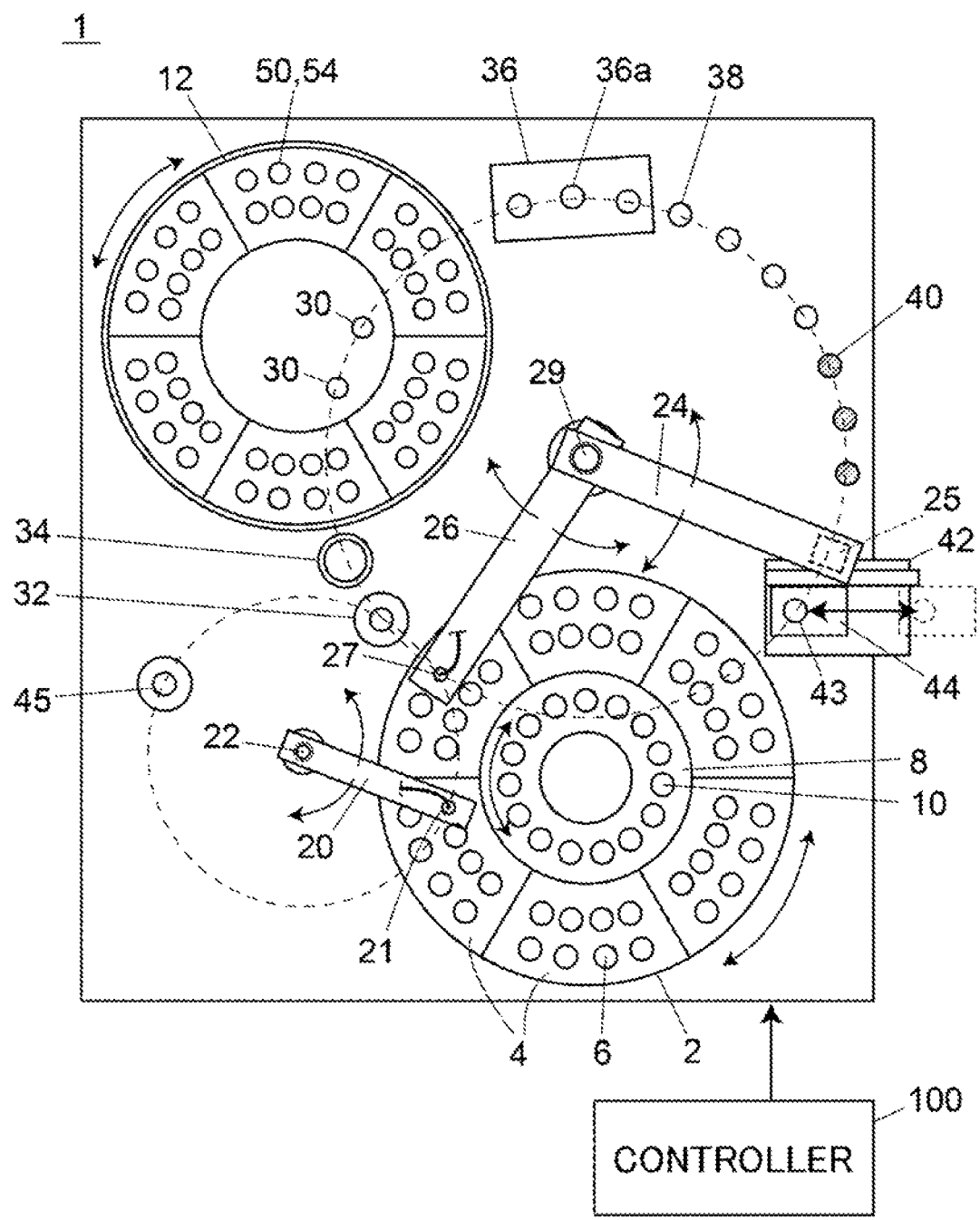
FIG. 1 is a plan view showing a deproteinization processing part of an embodiment of a culture medium processing system.

FIG. 1 shows an example of the deproteinization processing part of the culture medium processing system.

A deproteinization processing part 1 deproteinizes the culture medium using an extraction device including a filtration container 50 and a collection container 54. The filtration container 50 and the collection container 54 are transported by a transport arm 24. The transport arm 24 has a holding part 25 for holding the filtration container 50 and the collection container 54 at the distal end, and the holding part 25 rotates in a horizontal plane around a vertical shaft 29 holding its base end so as to draw an arc-shaped track.

A sample container setting place 2 at which a sample container 6 containing a culture medium as a sample is set is provided, and a sampling arm 20 (sample dispensing part) for sucking the culture medium from the sample container 6 set at the sample container setting place 2 and dispensing the culture medium into the filtration container 50 is provided in the vicinity thereof. A sample rack 4 that holds a plurality of sample containers 6 is set in the sample container setting place 2 in an annular shape. The sample container setting place 2 rotates in a horizontal plane so as to move the sample rack 4 in the circumferential direction, and a desired sample container 6 is disposed at a predetermined suction position by rotation of the sample container setting place 2. The suction position is a position along the track of a sampling nozzle 21 at the distal end of the sampling arm 20, and is a position at which the culture medium is sucked by the sampling nozzle 21.

The sampling arm 20 has a vertical shaft 22 passing through the base end thereof, and performs a rotation operation in a horizontal plane around the shaft 22 and an up and down movement along the shaft 22 in the vertical direction. The sampling nozzle 21 is held at the distal end of the sampling arm 20 so that the distal end thereof is directed vertically downward, and moves in an arc-shaped track in a horizontal plane and moves up and down in the vertical direction by the sampling arm 20.

A dispensing port 32 is provided at a position on the track of the sampling nozzle 21 and on the track of the holding part 25 of the transport arm 24. The dispensing port 32 is a sample dispensing position at which the sampling nozzle 21 dispenses the culture medium into the empty filtration container 50. The empty filtration container 50 is set at the dispensing port 32 by the transport arm 24. The dispensing port 32 is also a reagent dispensing position at which various reagents are added into the filtration container 50 containing the culture medium.

A reagent container setting place 8 at which a reagent container 10 is set is provided inside the sample container setting place 2, and a reagent arm 26 (reagent dispensing part) for taking a reagent from the reagent container 10 disposed in the reagent container setting place 8 is provided. The base end of the reagent arm 26 is supported by the vertical shaft 29 common to the transport arm 24, and rotates in a horizontal plane and moves up and down. A reagent nozzle 27 is provided at the distal end of the reagent arm 26. The reagent nozzle 27 is provided with its distal end directed vertically downward, and moves in a horizontal plane that draws the same arc-shaped track as the holding part 25 of the transport arm 24 and moves up and down. The reagent nozzle 27 has the base end that is connected to a syringe pump that sucks and discharges the liquid. The reagent nozzle 27 sucks and discharges the reagent from its distal end.

The reagent container setting place 8 rotates in a horizontal plane independently of the sample container setting place 2. A plurality of reagent containers 10 is disposed in an annular shape in the reagent container setting place 8, and the reagent container 10 is transported in the rotation direction by the rotation of the reagent container setting place 8, so that the desired reagent container 10 is disposed at a predetermined reagent taking position. The reagent taking position is a position along the track of the reagent nozzle 27 of the reagent arm 26 and is a position at which the reagent nozzle 27 sucks the reagent. The reagent nozzle 27 sucks a predetermined reagent, and then dispenses the sucked reagent into the filtration container 50 set at the dispensing port 32. The reagent placed in the reagent container setting place 8 includes a methanol solution, an acetonitrile solution, and an internal standard solution.

An extraction device setting place 12 is provided at a position different from that of the sample container setting place 2 and that of the reagent container setting place 8. The extraction device setting place 12 is configured to set a plurality of sets of extraction devices in an annular shape with the unused filtration container 50 and the collection containers 54 stacked with each other. The extraction device setting place 12 rotates in the horizontal plane to move the extraction device in the circumferential direction, and a set of the extraction device is disposed at a position along the track of the holding part 25 of the transport arm 24. The transport arm 24 can hold the unused filtration container 50 and/or the collection container 54 disposed at a position along the track of the holding part 25.

The filtration container 50 and the collection container 54 constituting the extraction device will be described with reference to FIGS. 2A, 2B, 3A, and 3B.

Figure 2A:
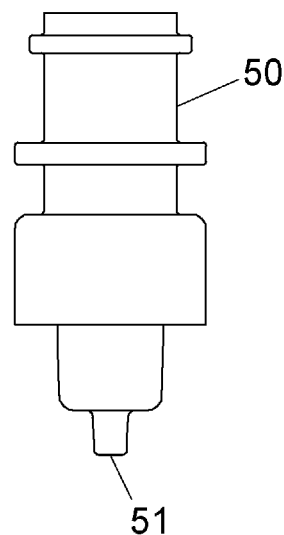
FIG. 2A is a front view showing an example of a filtration container of an extraction device used in the same embodiment.
Figure 2B:
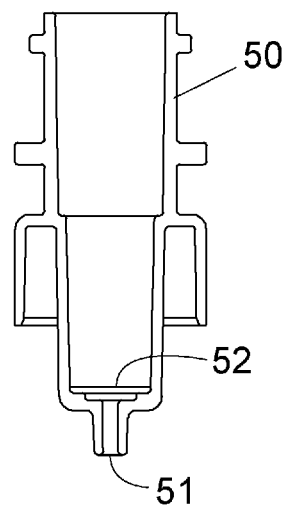
FIG. 2B is a cross-sectional view of the filtration container of FIG. 2A.
Figure 3A:
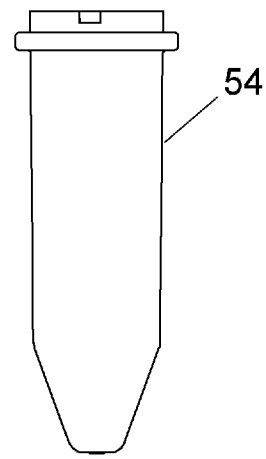
FIG. 3A is a front view showing an example of a collection container of the extraction device.
Figure 3B:
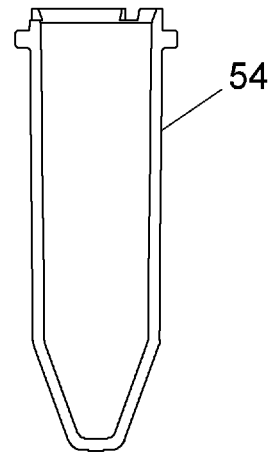
FIG. 3B is a cross-sectional view of the collection container of FIG. 3A.

As shown in FIGS. 2A and 2B, the filtration container 50 is a cylindrical container having an open top. A filtration filter 52 is provided at the bottom of the internal space, and an extraction port 51 for extracting the filtrate that has passed through the filtration filter 52 is provided at the lower end. THE filtration filter 52 is a filter for removing the protein contained in the culture medium as a sample by filtration, and is composed of PTFE, acrylic copolymer film, etc. As shown in FIGS. 3A and 3B, the collection container 54 accommodates the lower part of the filtration container 50, and is a cylindrical container for collecting the filtrate extracted from the extraction port 51 of the filtration container 50.

Returning to FIG. 1, the description will be continued. The deproteinization processing part 1 includes a filtration part 30, a stirring part 36, a temperature adjustment part 38, and a temperature adjustment part 40. The filtration part 30 is provided at two positions inside the extraction device setting place 12. The stirring part 36 includes three stirring ports 36a, and is for stirring the liquid inside the filtration container 50 set at the stirring port 36a. The temperature adjustment part 38 is for adjusting the temperature of the filtration container 50, and the temperature adjustment part 40 is for adjusting the temperature of the collection container 54. The temperature adjustment parts 38 and 40 are disposed side by side in the arc shape.

The filtration part 30 includes a filtration port at which an extraction device is set with the collection container 54 disposed immediately below the filtration container 50, that is, with the filtration container 50 stacked on the collection container 54. The filtration part 30 includes a mechanism that applies pressure (for example, negative pressure) to the liquid in the filtration container 50 set at the filtration port. The configuration of the mechanism that applies a negative pressure to the liquid in the filtration container 52 may be the same as that disclosed in Patent Literature 1.

The stirring part 36 has a mechanism that individually operates each stirring port 36a individually in a horizontal plane, and stirs the liquid inside the filtration container 50 disposed in each stirring port 36a. The configuration of the stirring part 36 may be the same as the configuration of the stirring part disclosed in Patent Literature 1.

The deproteinization processing part 1 further includes a transfer device 42 for transferring the filtrate collected in the collection container 54 to an LC part 200 (see FIG. 5) disposed adjacent to the deproteinization processing part 1. The transfer device 42 includes a moving part 44 that moves in the direction (the direction of the arrow in FIG. 1) in a horizontal plane by a drive mechanism having a rack and pinion mechanism. A transfer port 43 at which a collection container 54 containing the filtrate is set is provided on the upper surface of the moving part 44.

When the filtrate is not being transferred to the LC part 200, the transfer port 43 is disposed at a position along the track of the holding part 25 of the transport arm 24 (the position shown in the solid line), and in this position, the collection container 54 is set at the transfer port 43 by the transport arm 24, and the collection container 54 is collected from the transfer port 43.

In the vicinity of the dispensing port 32, a disposal port 34 at which the used filtration container 50 and the used collection container 54 are discarded is provided at a position along the track of the holding part 25 of the transport arm 24. A cleaning port 45 at which the sampling nozzle 21 is cleaned is provided at a position along the track of the sampling nozzle 21.

The operation of the sample container setting place 2, the reagent container setting place 8, the extraction device setting place 12, the sampling arm 20, the transport arm 24, the reagent arm 26, the filtration part 30, the stirring part 36, the temperature adjustment parts 38, 40, and the transfer device 42 of deproteinization processing part 1 is controlled by a controller 100. The controller 100 is, for example, a function obtained by executing a program in a computer circuit provided in the deproteinization processing part 1.

Figure 4:
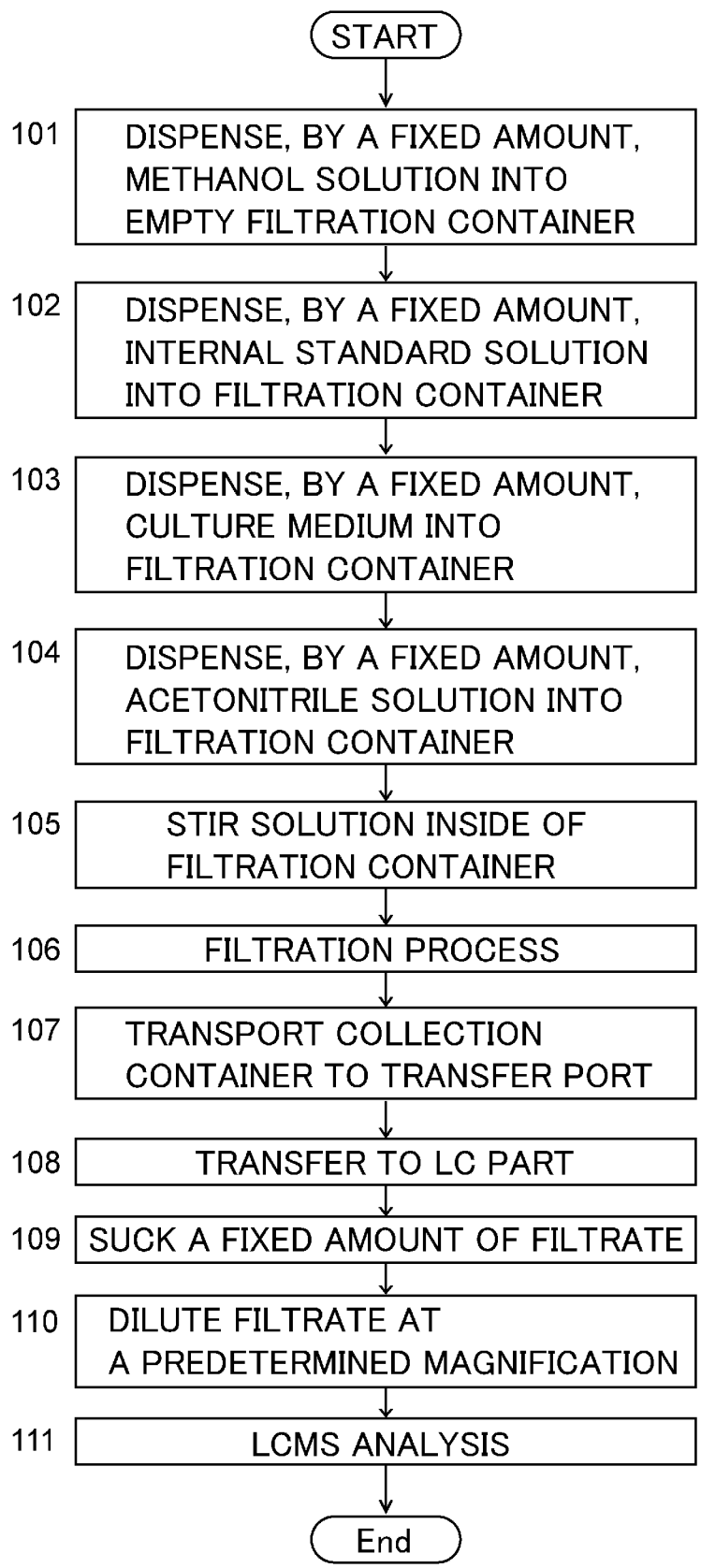
FIG. 4 is a flowchart for explaining the operation of the culture medium processing system of the same embodiment.

The flow from the deproteinization process of the culture medium to the LCMS analysis will be described using the flowchart of FIG. 4 together with FIG. 1.

First, the empty filtration container 50 is transported to the dispensing port 32 by the transport arm 24, and the methanol solution is dispensed as a conditioning agent into the filtration container 50 by the reagent nozzle 27 (step 101). Thereby, the filtration filter 52 in the filtration container 50 is conditioned. The dispensing amount of the methanol solution may be fixed irrespective of the type of culture medium on which the deproteinization process is performed. After that, the internal standard solution is dispensed into the filtration container 50 by the reagent nozzle 27 (step 102), and the culture medium as a sample is further dispensed by the sampling nozzle 21 (step 103). The dispensing amount of the internal standard solution and the dispensing amount of the sample here may be fixed irrespective of the type of the culture medium.

Furthermore, the reagent nozzle 27 dispenses the acetonitrile solution as a deproteinization agent (step 104). The dispensing amount of the deproteinization agent here may be fixed irrespective of the type of the culture medium.

Next, the transport arm 24 transports the filtration container 50 to the stirring port 36a of the stirring part 36, and stirs the liquid inside the filtration container 50 (step 105). After that, the transport arm 24 transports the filtration container 50 and the collection container 54 to the filtration port of the filtration part 30 so that the filtration container 50 is stacked on the collection container 54, and pressure is applied to the solution in the filtration container 50 to collect the filtrate in the collection container 54 (step 106). After the filtration process is completed, the used filtration container 50 is transported to the disposal port 34 by the transport arm 24 and discarded.

The collection container 54 collecting the filtrate is conveyed by the transport arm 24 to the transfer port 43 of the transfer device 42 (step 107), and the collection container 54 is transferred to the LC part 200 (step 108). In the LC part 200, a fixed amount of filtrate is sucked by the sampling needle (step 109), and the filtrate is diluted at a predetermined magnification (step 110). The diluted filtrate is injected into the analysis flow path for the liquid chromatography analysis, and the liquid chromatography mass spectrometry (LCMS analysis) is performed (step 111).

The present inventors have found in the experiments that a filtrate can be obtained with high recovery efficiency by using a methanol solution as a conditioning agent for the filtration filter 52 and using an acetonitrile solution as a deproteinization agent. The experimental data is shown in Table 1 below.

TABLE 1

| Culture medium type | Con: Methanol Dep: Methanol | Con: Acetonitrile Dep: Acetonitrile | Con: Methanol Dep: Acetonitrile |
| --- | --- | --- | --- |
| nTeSR1 | 300 μL (90.9%) | 80 μL (24.2%) | 283 μL (85.8%) |
| StemPRO | 135 μL (40.9%) | 40 μL (12.1%) | 300 μL (90.9%) |
| AK03N | 80 μL (24.2%) | 250 μL (75.8%) | 307 μL (93.0%) |
| FBS | 20 μL (6.06%) | 300 μL (90.9%) | 306 μL (92.7%) |

In the above experiment, the collection amount (and recovery rate) of the filtrate of each culture medium when a methanol solution is used as a conditioning agent (Con) and a deproteinization agent (Dep), when an acetonitrile solution is used as a conditioning agent (Con) and a deproteinization agent (Dep), and when a methanol solution is used as a conditioning agent (Con) and an acetonitrile solution is used as a deproteinization agent (Dep), was determined. In any case, 10 to 20 μL of the conditioning agent, 20 to 35 μL of the internal standard solution (pure water), 20 μL of the culture medium, and 240 to 280 μL of the deproteinization agent were dispensed into the filtration container 50, and the total amount of the solution in the filtration container 50 was adjusted to 310 to 330 μL.

As can be seen from Table 1, when a methanol solution was used as a conditioning agent (Con) and a deproteinization agent (Dep), while a good filtrate recovery rate was obtained for mTeSR1, the recovery rates for the other three media were low. When acetonitrile solution was used as a conditioning agent (Con) and a deproteinization agent (Dep), while a good filtrate recovery rate was obtained for the AK03N and FBS media, the recovery rates for the other two media were low. In contrast, when a methanol solution as a conditioning agent (Con) and an acetonitrile solution as a deproteinization agent (Dep) were used, good filtrate recovery rates were obtained for all media. From this, even when a methanol solution as a conditioning agent (Con) and an acetonitrile solution as a deproteinization agent (Dep) were used, and the dispensed volume of each of the conditioning agent, the culture medium, the internal standard solution, and the deproteinization agent to the filtration container 50 was fixed irrespective of the type of culture medium, it can be seen that a good filtrate recovery rate is obtained.

Based on the above findings, in this embodiment, a methanol solution is used as a conditioning agent for the filtration filter 52, an acetonitrile solution is used as a deproteinization agent, and the dispensed volume of each of the conditioning agent, the culture medium, the internal standard solution, and the deproteinization agent to the filtration container 50 is fixed irrespective of the type of culture medium. This eliminates the need for the user to set the type and the amount of the solution to be dispensed into the filtration container 50 for each type of culture medium, and makes it easy to set the dispensing conditions.

Figure 5:
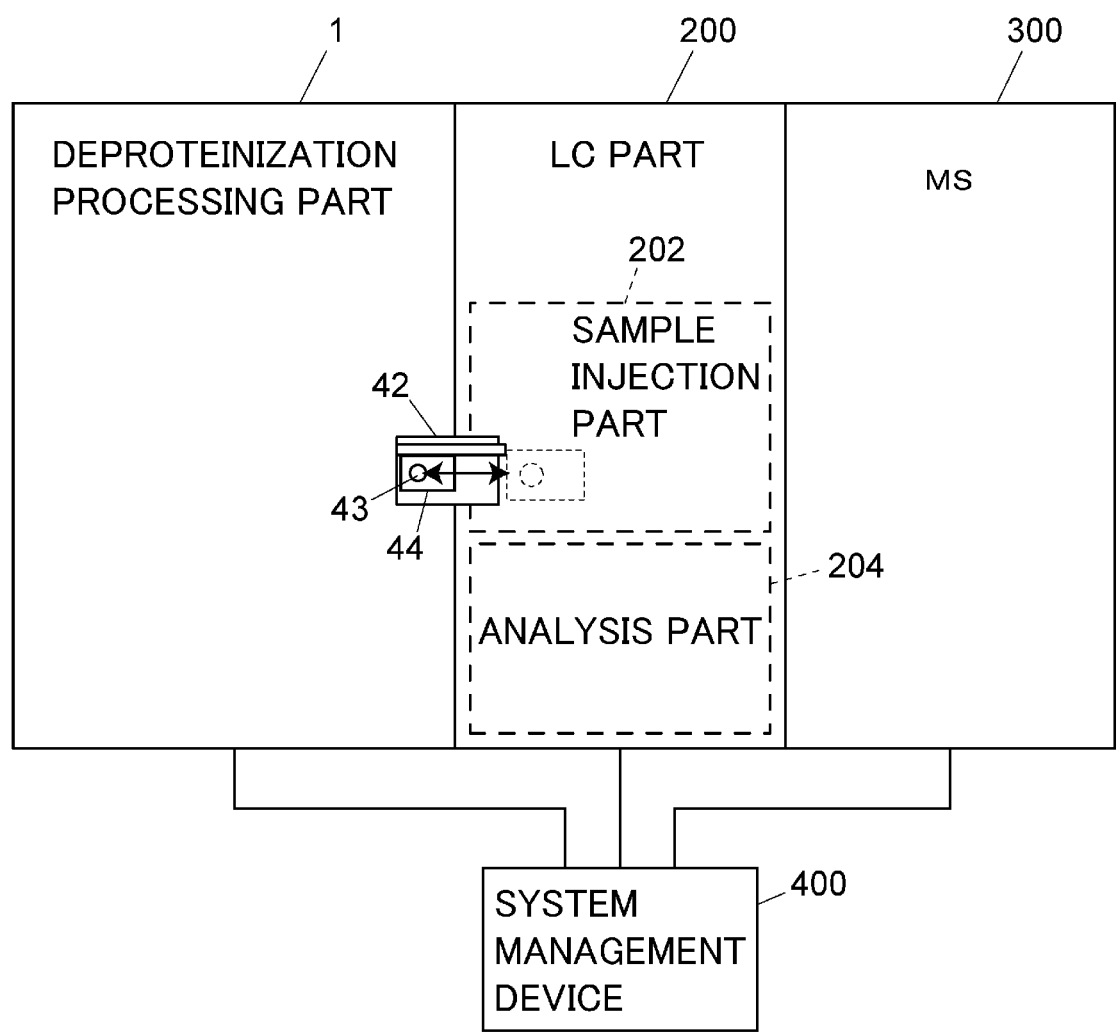
FIG. 5 is a schematic configuration diagram showing an example of the overall configuration of the culture medium processing system of the same embodiment.

Next, an example of the configuration of the entire culture medium processing system including the deproteinization processing part 1 will be described with reference to FIG. 5.

The LC part 200 is disposed adjacent to the deproteinization processing part 1 described in the above embodiment, and further, a mass spectrometer (MS) 200 is disposed adjacent to the LC part 200. The operation of the deproteinization processing part 1, the LC system 200, and the MS 300 is managed by a common system management device 400. The system management device 400 is a dedicated computer or general-purpose personal computer equipped with software for controlling and managing the deproteinization processing part 1, the LC system 200, and the MS 300.

The LC part 200 includes a sample injection part 202 and an analysis part 204. The sample injection part 202 is configured to take a fixed amount of filtrate from the collection container 54 transferred to the LC part 200 by the transfer device 42 of the deproteinization processing part 1, dilute the taken filtrate at a predetermined magnification, and inject it into an analysis flow path for liquid chromatography analysis. When the moving part 44 of the transfer device 42 moves to the LC part 200, the collection container 54 set at the transfer port 43 of the moving part 44 is disposed at a predetermined position in the sample injection part 202. The analysis part 204 is configured to perform liquid chromatography analysis of the filtrate injected by the sample injection part 202.

In the embodiment described above, although the culture medium processing system is configured by the deproteinization processing part 1, the LC part 200, the MS 300, and the system management device 400, the present invention is not limited to this. The culture medium processing system may be configured by some elements including the deproteinization processing part 1. Embodiments of the culture medium processing system and the culture medium processing method according to the present invention are as follows.

The embodiment of the culture medium processing system according to the present invention includes an extraction device including a filtration container and a collection container. The filtration container has an open upper surface, a filtration filter, disposed inside the filtration container, for deproteinizing a culture medium for cell culture, and an extraction port, disposed at a lower end of the filtration container, for extracting a filtrate downward that has passed through the filtration filter. The collection container is for collecting the filtrate extracted from the extraction port of the filtration container by being disposed immediately below the filtration container. The culture medium processing system further includes an extraction device setting place at which the extraction device is set in an empty state; a sample container setting place at which sample containers containing culture medium to be deproteinized as samples are set; a reagent container setting place at which reagent containers containing at least a methanol solution and an acetonitrile solution respectively as reagents are set; a sample dispensing part configured to suck a sample from a sample container set at the sample container setting place and dispense the sucked sample into the filtration container disposed at a predetermined sample dispensing position; a reagent dispensing part configured to suck desired reagents from the reagent containers set at the reagent container setting place and to dispense the sucked reagents into the filtration container disposed at a predetermined reagent dispensing position; a filtration part including a filtration port at which the extraction device is set with the collection container disposed immediately below the filtration container, where the filtration part is configured to collect a filtrate into the collection container by performing a filtration process for a solution in the filtration container of the extraction device set at the filtration port; a transport arm configured to hold the filtration container and/or the collection container of the extraction device set at the extraction device setting place and to transport the held filtration container and/or the held collection container to the sample dispensing position, the reagent dispensing position, and the filtration part; and a controller configured to control operation of the sample dispensing part, the reagent dispensing part and the transport arm to deproteinize a sample. The controller is configured to perform conditioning for the filtration filter by dispensing a methanol solution into the empty filtration container, then to dispense a sample into the filtration container add the acetonitrile solution as a deproteinization agent to the sample in the filtration container, and then to perform the filtration process in the filtration part.

In the first aspect of the embodiment of the culture medium processing system according to the present invention, since a methanol solution is used as a conditioning agent for conditioning the filtration filter, and an acetonitrile solution is used as a deproteinization agent, the filtrate can be collected at a high recovery rate irrespective of the type of the culture medium as a sample. For this reason, in the first aspect of the embodiment of the culture medium processing system according to the present invention, the controller can be configured to dispense a fixed amount of a methanol solution, a sample, and an acetonitrile solution into the filtration container irrespective of a type of the sample culture medium. According to such an embodiment, there is no need to adjust the dispensing condition for each liquid for each type of culture medium, and the setting operation of the dispensing condition is easy.

In the second aspect of the above embodiment of the culture medium processing system according to the present invention, a standard solution container containing an internal standard solution is set at the reagent container setting place, and the controller is configured to dispense the internal standard solution into the filtration container before dispensing a sample into the filtration container after performing the conditioning for the filtration filter. Although it is conceivable that when the culture medium is dispensed immediately after dispensing the methanol solution into the filtration container, a rapid reaction between the culture medium and the methanol may occur, and the deproteinization process is not performed normally, the rapid reaction between the culture medium and methanol is alleviated by dispensing the internal standard solution (for example, pure water) before dispensing the culture medium, and the deproteinization process can be performed normally. This second aspect can be combined with the first aspect.

In the second embodiment, the controller may be configured to dispense a fixed amount, which is irrespective of a type of the culture medium which is the sample, of the internal standard solution into the filtration container.

In the third aspect of the above embodiment of the culture medium processing system according to the present invention, the culture medium processing system further includes an LC part including a sample injection part and an analysis part. The sample injection part is configured to suck a fixed amount of a filtrate collected in the collection container by the filtration process and to injecting the filtrate into an analysis flow path for a liquid chromatography analysis. The analysis part is configured to perform a liquid chromatography analysis of the filtrate injected into the analysis flow path by the sample injection part. In the culture medium processing system of the present invention, when the deproteinization process is performed, since a methanol solution is used as a conditioning agent for the filtration filter, and acetonitrile solution is used as a deproteinization agent, the high filtrate recovery rate is obtained. Therefore, since the amount of filtrate necessary for analysis is reliably collected in the collection container, it is possible to reliably suck a fixed amount of filtrate and inject it into the analysis flow path. This third aspect can be freely combined with the first and second aspects.

In the third aspect, the sample injection part may be configured to dilute the fixed amount of filtrate sucked from the collection container at a predetermined magnification.

In the embodiment of the culture medium processing method according to the present invention, the method uses an extraction device including a filtration container and a collection container. The filtration container has an open upper surface, a filtration filter, disposed inside the filtration container, for deproteinizing a culture medium for cell culture, and an extraction port, disposed at a lower end of the filtration container, for extracting a filtrate downward that has passed through the filtration filter. The collection container is for collecting the filtrate extracted from the extraction port of the filtration container by being disposed immediately below the filtration container. The method of processing the culture medium includes, in the sequence set forth: a conditioning step of dispensing a methanol solution into the empty filtration container to condition the filtration filter; a sample dispensing step of dispensing a culture medium as a sample into the filtration container; a deproteinization agent dispensing step of adding an acetonitrile solution as a deproteinization agent to the sample in the filtration container; and a filtration step of filtering a solution in the filtration container with the collection container disposed immediately below the filtration container to collect the filtrate in the collection container.

In the above embodiment of the culture medium processing method according to the present invention, since a methanol solution is used as a conditioning agent for conditioning the filtration filter, and an acetonitrile solution is used as a deproteinization agent, the filtrate can be collected at a high recovery rate irrespective of the type of the culture medium as a sample. Therefore, in the first aspect of the embodiment of the culture medium processing method according to the present invention, each of an amount of a methanol solution to be dispensed into the filtration container in the conditioning step, an amount of a sample to be dispensed into the filtration container in the sample dispensing step, and an amount of an acetonitrile solution to be dispensed into the filtration container in the deproteinization agent dispensing step can be fixed irrespective of a type of the sample culture medium. According to such an embodiment, there is no need to adjust the dispensing condition for each liquid for each type of culture medium, and the setting operation of the dispensing condition is easy.

In the second aspect of the above embodiment of the culture medium processing method according to the present invention, the method further includes a standard solution dispensing step of dispensing an internal standard solution into the filtration container before the sample dispensing step after the conditioning step. The rapid reaction between the culture medium and methanol is alleviated by dispensing the internal standard solution (for example, pure water) before dispensing the culture medium on the filtration filter conditioned by methanol, and the deproteinization process can be performed normally. This second aspect can be combined with the first aspect.

In the second embodiment, the standard solution dispensing step can include dispensing a fixed amount, which is irrespective of a type of the sample culture medium, of the internal standard solution into the filtration container.

In the third aspect of the embodiment of the culture medium processing method according to the present invention, the method further includes an injection step of sucking a fixed amount of a filtrate collected in the collection container in the filtration step after the filtration step, and then injecting the sucked filtrate into an analysis flow path for liquid chromatography, and an analysis step of performing a liquid chromatography analysis of the filtrate injected into the analysis flow path in the filtrate injection step. In the culture medium processing method of the present invention, when the deproteinization process is performed, since a methanol solution is used as a conditioning agent for the filtration filter, and acetonitrile solution is used as a deproteinization agent, the high filtrate recovery rate is obtained. Therefore, since the amount of filtrate necessary for analysis is reliably collected in the collection container, it is possible to reliably suck a fixed amount of filtrate and inject it into the analysis flow path. This third aspect can be freely combined with the first and second aspects.

In the third aspect, the injection step may include sucking the fixed amount of the filtrate collected in the collection container, and then diluting the filtrate at a predetermined magnification.

REFERENCE SIGNS LIST

1: deproteinization processing part
2: sample container setting place
4: sample rack
6: sample container
8: reagent container setting place
10: reagent container
12: extraction device setting place
20: sampling arm
21: sampling nozzle
22, 29: shaft
24: transport arm
25: holding part
26: reagent arm
27: reagent nozzle
30: filtration part
32: dispensing port
34: disposal port
36: stirring part
36a: stirring port
38, 40: temperature adjustment part
42: transfer device
43: transfer port
44: moving part
45: cleaning port
50: filtration container
51: extraction port
52: filtration filter
54: collection container
100: controller
200: LC part
202: sample injection part
204: analysis part
300: MS
400: system management device

What is claimed is:

1. A culture medium processing system comprising:
an extraction device including a filtration container and a collection container, wherein the filtration container has an open upper surface, a filtration filter, disposed inside the filtration container, for deproteinizing a culture medium for cell culture, and an extraction port, disposed at a lower end of the filtration container, for extracting a filtrate downward that has passed through the filtration filter, the collection container being for collecting the filtrate extracted from the extraction port of the filtration container by being disposed immediately below the filtration container;
an extraction device setting place at which the extraction device is set in an empty state;
a sample container setting place at which sample containers containing culture medium to be deproteinized as samples are set;
a reagent container setting place in which reagent containers, which include a container containing a methanol solution as a reagent and a container containing an acetonitrile solution as a reagent, are set;
a sample dispensing part configured to suck a sample from a sample container set at the sample container setting place and dispense the sucked sample into the filtration container disposed at a predetermined sample dispensing position;
a reagent dispensing part configured to suck desired reagents from the reagent containers set at the reagent container setting place and to dispense the sucked reagents into the filtration container disposed at a predetermined reagent dispensing position;
a stirring part including a stirring port at which the filtration container is set, the stirring part being configured to stir a liquid inside the filtration container set in the stirring port,
a filtration part including a filtration port at which the extraction device is set with the collection container disposed immediately below the filtration container, the filtration part being configured to collect a filtrate into the collection container by performing a filtration process for a solution in the filtration container of the extraction device set at the filtration port;
a transport arm configured to hold the filtration container and/or the collection container of the extraction device set at the extraction device setting place and to transport the held filtration container and/or the held collection container to the sample dispensing position, the reagent dispensing position, the stirring part, and the filtration part; and
a controller configured to control operation of the sample dispensing part, the reagent dispensing part and the transport arm to deproteinize a sample,
wherein the controller is configured to perform conditioning for the filtration filter, the deproteinization, and then the filtration process in the filtration part, the conditioning is performed by sucking the methanol solution from the container containing the methanol solution and dispensing a first amount of the sucked methanol solution into the empty filtration container so as to wet the filtration filter which has been dry, after the conditioning, the deproteinization is performed by dispensing a second amount of a sample into the filtration container and by sucking the acetonitrile solution from the container containing the acetonitrile solution, dispensing a third amount, which is larger than the first amount and second amount, of the acetonitrile solution as a deproteinization agent into the filtration container and stirring the sample and the acetonitrile solution in the filtration container.

2. The culture medium processing system according to claim 1, wherein the first amount, the second amount, and the third amount are each fixed amount.

3. The culture medium processing system according to claim 1, wherein a standard solution container containing an internal standard solution is set at the reagent container setting place, and the controller is configured to dispense the internal standard solution into the filtration container before dispensing a sample into the filtration container after performing the conditioning for the filtration filter.

4. The culture medium processing system according to claim 3, wherein the controller is configured to dispense a fixed amount of the internal standard solution into the filtration container.

5. The culture medium processing system according to claim 1, further comprising an LC part including a sample injection part and an analysis part, wherein the sample injection part is configured to suck a fixed amount of a filtrate collected in the collection container by the filtration process and to injecting the filtrate into an analysis flow path for a liquid chromatography analysis, and the analysis part is configured to perform a liquid chromatography analysis of the filtrate injected into the analysis flow path by the sample injection part.

6. The culture medium processing system according to claim 5, wherein the sample injection part is configured to dilute the fixed amount of filtrate sucked from the collection container at a predetermined magnification.

7. A method of processing a culture medium using an extraction device, the extraction device including a filtration container having an open upper surface, a filtration filter, disposed inside the filtration container, for deproteinizing a culture medium for cell culture, and an extraction port, disposed at a lower end of the filtration container, for extracting a filtrate downward that has passed through the filtration filter, and a collection container for collecting the filtrate extracted from the extraction port of the filtration container by being disposed immediately below the filtration container, the method of processing the culture medium comprising, in the sequence set forth:

a conditioning step of dispensing a first amount of a methanol solution into the empty filtration container to wet the filtration filter which has been dry;

a sample dispensing step of dispensing a second amount of a culture medium as a sample into the filtration container;

a deproteinization agent dispensing step of dispensing a third amount, which is larger than the first amount and the second amount, of an acetonitrile solution as a deproteinization agent into the filtration container including the filtration filter conditioned by the methanol solution so as to add the acetonitrile solution to the sample in the filtration container;

a stirring step of stirring a liquid in the filtration container after the deproteinization agent dispensing step; and a filtration step of filtering a solution in the filtration container with the collection container disposed immediately below the filtration container to collect the filtrate in the collection container.

8. The method of processing the culture medium according to claim 7, wherein the first amount, the second amount, and the third amount are each fixed amounts.

9. The method of processing the culture medium according to claim 7, further comprising a standard solution dispensing step of dispensing an internal standard solution into the filtration container before the sample dispensing step after the conditioning step.

10. The method of processing the culture medium according to claim 9, wherein the standard solution dispensing step includes dispensing a fixed amount of the internal standard solution into the filtration container.

11. The method of processing the culture medium according to claim 7, further comprising:

an injection step of sucking a fixed amount of a filtrate collected in the collection container in the filtration step after the filtration step, and then injecting the sucked filtrate into an analysis flow path for liquid chromatography; and an analysis step of performing a liquid chromatography analysis of the filtrate injected into the analysis flow path in the filtrate injection step.

12. The method of processing the culture medium according to claim 11, wherein the injection step includes sucking the fixed amount of the filtrate collected in the collection container, and then diluting the filtrate at a predetermined magnification.

* * * * *